US012617739B2

(12) United States Patent
Hirohata et al.

(10) Patent No.: US 12,617,739 B2
(45) Date of Patent: May 5, 2026

(54) METHOD FOR PRODUCING PARA-XYLENE

(71) Applicant: CHIYODA CORPORATION, Yokohama (JP)

(72) Inventors: Osamu Hirohata, Yokohama (JP); Tadashi Ito, Yokohama (JP); Taichiro Masagaki, Yokohama (JP); Yuria Watanabe, Yokohama (JP)

(73) Assignee: CHIYODA CORPORATION, Yokohama (JP)

( * ) Notice: Subject to any disclaimer, the term of this patent is extended or adjusted under 35 U.S.C. 154(b) by 0 days.

(21) Appl. No.: 18/556,902

(22) PCT Filed: Mar. 23, 2022

(86) PCT No.: PCT/JP2022/013653
§ 371 (c)(1),
(2) Date: Oct. 24, 2023

(87) PCT Pub. No.: WO2022/230467
PCT Pub. Date: Nov. 3, 2022

(65) Prior Publication Data

US 2024/0217893 A1 Jul. 4, 2024

(30) Foreign Application Priority Data

Apr. 30, 2021 (JP) ............................ JP2021-078065

(51) Int. Cl.
*C07C 1/12* (2006.01)
*C07C 1/04* (2006.01)
*C07C 7/00* (2006.01)

(52) U.S. Cl.
CPC .................. *C07C 1/12* (2013.01); *C07C 1/04* (2013.01); *C07C 7/005* (2013.01)

(58) Field of Classification Search
CPC .. C07C 1/12; C07C 1/104; C07C 7/09; C07C 2523/06; C07C 2523/26; C07C 2523/72;
(Continued)

(56) References Cited

U.S. PATENT DOCUMENTS 2,297,537 A * 9/1942 Rich ........................ C10G 7/00 562/606
5,100,635 A * 3/1992 Krishnamurthy .......... F25J 3/08 423/247

(Continued)

FOREIGN PATENT DOCUMENTS

CN 106518591 A 3/2017
JP S58-035128 A 3/1983

(Continued)

OTHER PUBLICATIONS

International Search Report dated Jun. 14, 2022, issued in counterpart Application No. PCT/JP2022/013653, with English Translation. (6 pages).

(Continued)

*Primary Examiner* — Thuan D Dang
(74) *Attorney, Agent, or Firm* — WHDA, LLP

(57) ABSTRACT

The method is for producing para-xylene using, as a main raw material, a mixed gas of carbon dioxide or carbon monoxide or both thereof and hydrogen. The method including: a reaction step of bringing a raw material mixed gas including the mixed gas into contact with a reaction catalyst under high temperature and high pressure to cause a reaction, to thereby obtain a product gas mixture containing para-xylene; a separation step of cooling the product gas mixture obtained in the reaction step to condense a high boiling point component, to thereby separate the product gas mixture into a water phase containing a water-soluble component, an oil phase containing a xylene mixture, and a gas phase containing an unreacted gas; and a circulation step of (Continued)

mixing at least part of the gas phase having been separated in the separation step into the raw material mixed gas.

8 Claims, 6 Drawing Sheets

(58) Field of Classification Search
CPC ... C07C 2529/40; C07C 1/043; C07C 1/0435; B01J 7/005; B01J 23/005; B01J 23/26; B01J 2209/186; B01J 23/868; B01J 29/005; B01J 29/405; B01J 35/19; B01J 29/035; B01J 29/40; B01J 29/80; B01J 2229/123; B01J 2229/32; B01J 2229/60; Y02P 20/52
See application file for complete search history.

(56) References Cited

U.S. PATENT DOCUMENTS

| | | | | |
|---|---|---|---|---|
| 5,877,368 | A | 3/1999 | Kiyama et al. | |
| 2013/0126038 | A1* | 5/2013 | Jamal | H01M 8/0618 429/411 |
| 2013/0150640 | A1* | 6/2013 | Ding | C07C 2/864 585/300 |
| 2020/0048159 | A1* | 2/2020 | Mikalsen | A01K 63/04 |
| 2020/0307997 | A1* | 10/2020 | Tranier | C01B 3/56 |

FOREIGN PATENT DOCUMENTS

| | | | |
|---|---|---|---|
| JP | H08-157399 | A | 6/1996 |
| JP | 2009-120897 | A | 6/2009 |
| JP | 2015-507612 | A | 3/2015 |
| JP | 2015-189721 | A | 11/2015 |
| JP | 2019-205969 | A | 12/2019 |
| JP | 2020-535966 | A | 12/2020 |
| RU | 2114811 | C1 | 7/1998 |
| WO | 2023/120628 | A1 | 6/2023 |

OTHER PUBLICATIONS

Written Opinion dated Jun. 14, 2022, issued in counterpart Application No. PCT/JP2022/013653. (4 pages).
Extended (Supplementary) European Search Report dated Aug. 28, 2023, issued in counterpart EP application No. 22782809.2. (8 pages).
Notification of Transmittal of Copies of Translation of the International Preliminary Report on Patentability (Form PCT/IB/338) issued in counterpart International application No. PCT/JP2022/013653 mailed Nov. 9, 2023 with Forms PCT/IB/373 and PCT/ISA/237. (12 pages).
Peipei Zhang et al., "One-pass selective conversion of syngas to paraxylene", Chemical Science, The Royal Society of Chemistry, Oct. 2017, vol. 8, pp. 7941-7946. (7 pages).
Office Action dated Aug. 21, 2025, issued in counterpart IN Application No. 202347079228, with English translation. (7 pages).
Office Action dated Nov. 22, 2025, issued in counterpart CN Application No. 202280031378.0, with English translation. (13 pages).

* cited by examiner

METHOD FOR PRODUCING PARA-XYLENE

TECHNICAL FIELD

The present invention relates to a method of producing para-xylene using, as a main raw material, a mixed gas of carbon dioxide or carbon monoxide and hydrogen.

BACKGROUND ART

Para-xylene, which is useful as a raw material for a polyester fiber or a polyethylene terephthalate (PET) resin, has hitherto been produced through a reforming reaction of naphtha in a petrochemical complex. However, this method requires fossil (petroleum) resources, and entails emission of carbon dioxide in a large amount in a production process.

Meanwhile, as a method of producing para-xylene without use of fossil resources, there has already been a proposal of a method involving using a so-called synthesis gas formed of carbon monoxide and hydrogen as a raw material (Non Patent Literature 1 and Patent Literature 1). This method involves converting the synthesis gas into methanol with, for example, a catalyst having a $ZnCr_2O_4$ spinel structure, followed by converting methanol into an aromatic compound containing para-xylene with, for example, a catalyst in which an outer surface of H-ZSM-5 zeolite (proton-type ZSM-5 zeolite) is coated with silicalite-1. Moreover, para-xylene is synthesized from carbon monoxide and hydrogen through a one-stage reaction operation by using those catalysts as a mixture. In addition, there is also a proposal of a method involving synthesizing para-xylene in one stage by using carbon dioxide, which is used instead of carbon monoxide, and hydrogen as raw materials (Patent Literature 2). In the method of Patent Literature 2, while production efficiency of para-xylene is improved by using a chromium oxide catalyst and a catalyst in which H-ZSM-5 zeolite is coated with silicalite-1 as a methanol synthesis catalyst and a para-xylene synthesis catalyst, respectively, para-xylene is synthesized from carbon dioxide and hydrogen through a one-stage reaction operation by using the methanol synthesis catalyst and the para-xylene synthesis catalyst as a mixture.

CITATION LIST

Patent Literature

PTL 1: Japanese Patent Translation Publication No. 2020-535966

PTL 2: Japanese Patent Application Laid-Open No. 2019-205969

Non Patent Literature

NPL 1: Peipei Zhang et al., Chemical Science, The Royal Society of Chemistry, October 2017, Vol. 8, 7941-7946

SUMMARY OF INVENTION

Technical Problem

In Example 1 of Patent Literature 2, para-xylene is synthesized at a high yield from a mixed gas of carbon dioxide and hydrogen by using a mixed catalyst of: a catalyst containing chromium oxide; and a catalyst containing H-ZSM-5 zeolite coated with silicalite-1. Meanwhile, a catalyst containing chromium zinc oxide is used instead of the catalyst containing chromium oxide in Comparative Example 1, and a catalyst containing a product in which acid sites of H-ZSM-5 coated with silicalite-1 are partially doped (ion exchanged) with zinc is further used in Comparative Example 2. However, the yield of para-xylene is 7.61% even in Example 1. The yield is higher than 3.42% of Comparative Example 1 and 5.06% of Comparative Example 2, but is not so different from those of Comparative Examples in that a $CO_2$ conversion rate is low. Accordingly, it is required to achieve an increase in yield of para-xylene and a reduction in consumption energy in the whole process including reutilizing an unreacted gas.

Solution to Problem

According to the present invention, there is provided a method of producing para-xylene using, as a main raw material, a mixed gas of carbon dioxide or carbon monoxide or both thereof and hydrogen, the method including: a reaction step of bringing a raw material mixed gas including the mixed gas into contact with a reaction catalyst under high temperature and high pressure to cause a reaction, to thereby obtain a product gas mixture containing para-xylene; a separation step of cooling the product gas mixture obtained in the reaction step to condense a high boiling point component, to thereby separate the product gas mixture into a water phase containing a water-soluble component, an oil phase containing a xylene mixture, and a gas phase containing an unreacted gas; and a circulation step of mixing at least part of the gas phase having been separated in the separation step into the raw material mixed gas. Thus, the above-mentioned objects can be achieved.

Advantageous Effects of Invention

According to the method of the present invention, ZSM-5-based zeolite coated with a compound containing silicon (preferably silicalite-1) is used as the catalyst in the reaction step, and hence the ratio of para-xylene in the oil phase having been separated from the product gas mixture in the separation step is increased, and less energy is required for a purification step (distillation, adsorption separation, isomerization, or disproportionation). In addition, the unreacted gas (carbon dioxide, carbon monoxide, and hydrogen), which makes up the majority of (volume of) the gas contained in the gas phase having been separated in the separation step, is returned to the reaction step, and hence the yield of para-xylene in the whole process is significantly increased.

DESCRIPTION OF EMBODIMENTS

Figure 1:
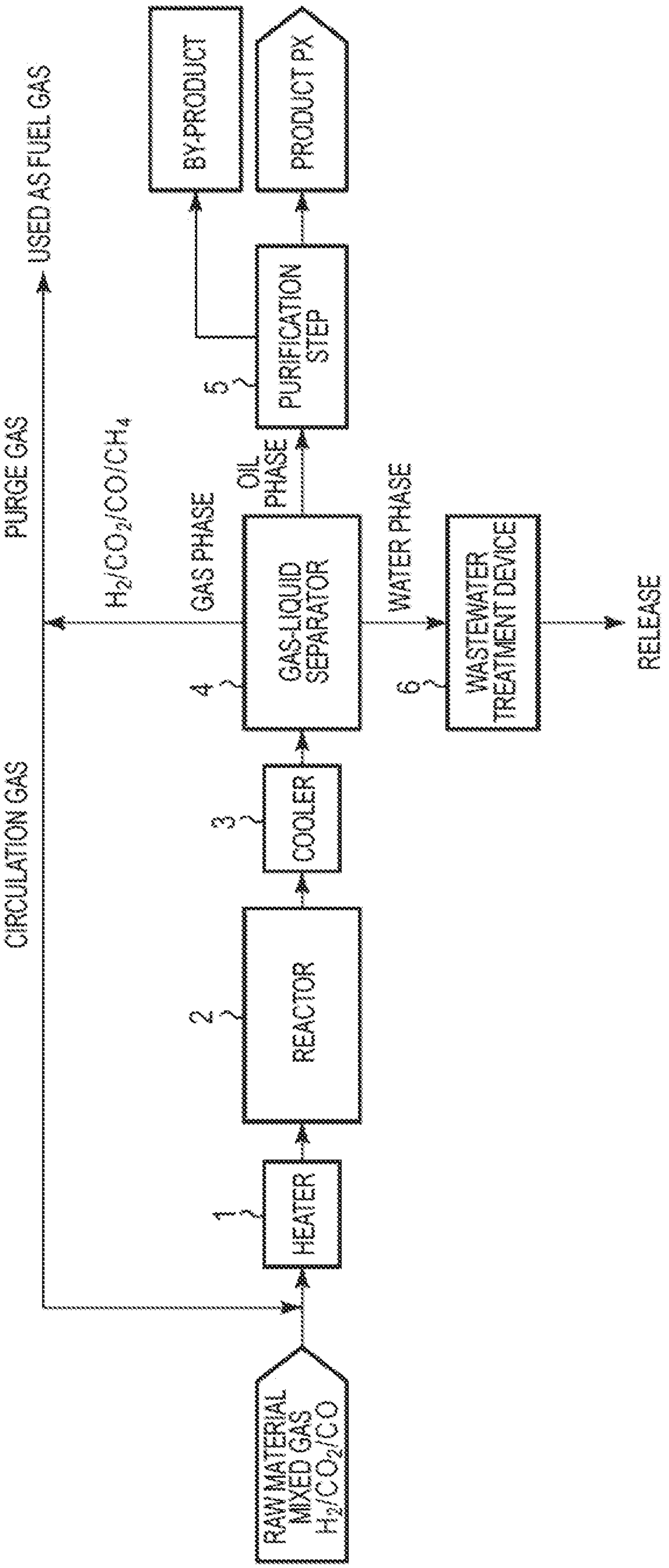
FIG. 1 is a diagram for illustrating an example (first embodiment) of an apparatus suitable for performing a method of the present invention.

A method of the present invention is a method of producing para-xylene using, as a main raw material, a mixed gas of carbon dioxide or carbon monoxide or both thereof and hydrogen, the method including: a reaction step of bringing a raw material mixed gas containing the mixed gas into contact with a reaction catalyst under high temperature and high pressure to cause a reaction, to thereby obtain a product gas mixture containing para-xylene; a separation step of cooling the product gas mixture obtained in the reaction step to condense a high boiling point component, to thereby separate the product gas mixture into a water phase containing a water-soluble component, an oil phase containing a xylene mixture, and a gas phase containing an unreacted gas; and a circulation step of mixing at least part of the gas phase having been separated in the separation step into the raw material mixed gas.

<Reaction Step>

When a product containing para-xylene is produced from a mixture of carbon monoxide and hydrogen, that is, a synthesis gas, it is considered that methanol or dimethyl ether is generated through hydrogenation of carbon monoxide as represented by the formula (1), and a mixture of various aromatic compounds is generated from methanol or dimethyl ether thus generated through lower olefins as represented by the formula (2).

$$2CO + 2H_2 \rightarrow 2CH_3OH\ (\leftrightarrow CH_3OCH_3 + H_2O) \tag{1}$$

$$CH_3OCH_3 \rightarrow C_2H_4, C_3H_6, \text{and the like} \rightarrow \text{various aromatic compounds} \tag{2}$$

In this case, a catalyst being formed of a composite oxide of zinc (or copper) and chromium and having a spinel structure may be suitably used as a catalyst for advancing the methanol synthesis reaction of the formula (1), and Zn/H-ZSM-5 zeolite may be suitably used as a catalyst for advancing the reaction of the formula (2) to selectively synthesize para-xylene. In this connection, when the outer surface of Zn/H-ZSM-5 zeolite is coated with a compound containing silicon (preferably one having the same lattice structure as ZSM-5 zeolite and having no acid site, such as silicalite-1), the ratio of para-xylene in a product mixture can be increased. When those catalysts are used as a mixture, the reaction of the formula (1) and the reaction of the formula (2) progress continuously or in parallel, and hence the product containing para-xylene can be produced in a one-stage reactor.

Meanwhile, when the product containing para-xylene is produced by using a mixed gas of carbon dioxide and hydrogen as a main raw material, a reaction for generating methanol progresses as represented by the formula (3).

$$CO_2 + 3H_2 \rightarrow CH_3OH + H_2O \tag{3}$$

That is, the amount of water generated as a by-product during the generation of methanol is increased. Accordingly, the yield of para-xylene can be increased more when the catalyst formed of chromium oxide (free of zinc or copper) is used as a catalyst for advancing the reaction of the formula (3), instead of the above-mentioned catalyst formed of a composite oxide of zinc (or copper) and chromium, and proton-type H-ZSM-5, which is not doped with zinc, is used as the catalyst for advancing the reaction of the formula (2), as described in Patent Literature 2.

That is, in the reaction step of the present invention, a catalyst containing an oxide of at least one kind of metal appropriately selected from chromium, zinc, and copper, and a catalyst containing H-ZSM-5 zeolite appropriately doped with zinc or the like and coated with a compound containing silicon, such as silicalite-1, may be combined and used as a mixture depending on a ratio between carbon dioxide and carbon monoxide in the mixed gas (hereinafter referred to as "raw material mixed gas") to be used as a main raw material and the content of another component therein. Herein, proton-type H-ZSM-5 zeolite and H-ZSM-5 zeolite doped (ion exchanged) with various ions are collectively referred to as ZSM-5-based zeolite, but ZSM-5-based zeolite coated with a compound containing silicon, such as silicalite-1, is preferably used in order to selectively synthesize para-xylene in the reaction of the formula (2). As described later, a gas phase component (including unreacted carbon dioxide and carbon monoxide) having been separated in the separation step is returned to the reaction step in the present invention, and hence it is required that the ratio between carbon dioxide and carbon monoxide and the content of the other component described above be considered at an inlet of a reactor.

One of the objects of the present invention is to contribute to a reduction in concentration of carbon dioxide in the atmosphere, and hence it is preferred to utilize, as carbon dioxide forming the raw material mixed gas, for example, carbon dioxide separated from an exhaust gas of an apparatus in which a fuel that generates carbon dioxide is combusted, such as a thermal power plant or various heating furnaces, carbon dioxide separated in an ammonia production apparatus, an ethylene glycol production apparatus, or a hydrogen production apparatus, carbon dioxide separated from a product gas of a gasification furnace for coal, biomass, or garbage, carbon dioxide separated from a blast furnace of an ironworks, or carbon dioxide separated from air in the atmosphere.

In addition, it is preferred to use, as hydrogen forming the raw material mixed gas, hydrogen generated through electrolysis of water with electric power generated by renewable energy, such as solar power, wind power, water power, geothermal power, or biomass, or by nuclear power.

In particular, it is preferred to use, as the raw material mixed gas, for example, a synthesis gas generated from a gasification furnace, an off-gas discharged from a blast furnace of an ironworks, an off-gas separated in a hydrogen production apparatus, a synthesis gas generated through co-electrolysis of water and carbon dioxide, or a synthesis gas generated through a reverse shift reaction between hydrogen and carbon dioxide.

The form of the reactor is not particularly limited as long as the reactor enables a gas-solid contact operation between the raw material mixed gas (gas) and the reaction catalyst (solid), and can maintain a desired temperature and a desired pressure (a packed bed, a moving bed, a fluidized bed, or the like). Of those, a packed bed is preferred in that contact efficiency is satisfactory, less channeling occurs, and mechanical damage to catalyst particles is also small. While the packing amount of the catalyst and the flow rate of the gas may be appropriately set, in the case of a packed bed form, the packing amount of the catalyst and the flow rate of the gas are desirably set so as to give a space velocity (SV) of from about 100/hr to about 10,000/hr in terms of a superficial velocity. In addition, a reaction temperature and a reaction pressure are preferably set to from about 250° C. to about 600° C. and from about 1 MPaG to about 10 MPaG, respectively.

<Separation Step>

The gas mixture containing para-xylene obtained in the reaction step is cooled in the separation step in the subsequent stage to condense the high boiling point component containing para-xylene. A liquid phase is further divided into a water phase containing a water-soluble component generated through the reactions, such as water or an alcohol, and an oil phase containing an aromatic component or the like (including para-xylene) immiscible with water. That is, the contents of a gas-liquid separator are divided into the water phase serving as a lower layer, the oil phase serving as a middle layer, and a gas phase serving as an upper layer in the stated order from a bottom side of the separator, and hence it is appropriate to extract fluids of the respective phases from the corresponding layer formation positions to an outside of the device. Alternatively, it is also appropriate to first separate a gas-liquid mixture into a gas phase and a liquid phase, and then separate the liquid phase into an oil phase and a water phase by a separation method utilizing a difference in specific gravity, such as centrifugal separation or sedimentation separation.

<Purification Step>

The oil phase having been extracted from the gas-liquid separator also contains, in addition to para-xylene serving as a target compound, other aromatic compounds, such as benzene, toluene, ortho-xylene, meta-xylene, ethylbenzene, and trimethylbenzene, and hence these aromatic compounds are separated as required. Accordingly, it is preferred to subject the oil phase to a distillation operation first, to thereby separate benzene and toluene each having a lower boiling point than xylenes (ortho-xylene, meta-xylene, para-xylene, and ethylbenzene) as low boiling point components, and also separate trimethylbenzene having a higher boiling point than the xylenes as a high boiling point component. Meanwhile, ortho-xylene, meta-xylene, and ethylbenzene each have a boiling point close to that of para-xylene, and hence it is inefficient to separate these compounds only through a distillation operation. In view of the foregoing, it is preferred to obtain a xylene fraction as a mixture of those compounds, and then subject the mixture to adsorption separation with zeolite.

Zeolite has pores each having the molecular size of para-xylene, and hence adsorbs para-xylene well, but hardly adsorbs ortho-xylene, meta-xylene, and ethylbenzene, and functions as a molecular sieve. That is, components (ortho-xylene, meta-xylene, and other impurities) other than para-xylene pass through an adsorption column without being adsorbed on zeolite, and hence when the mixture is repeatedly subjected to adsorption and desorption through use of zeolite, para-xylene can be concentrated and purified. Specifically, a xylene mixture is caused to flow through an adsorption column having an adsorbent (zeolite) packed therein to allow only para-xylene to be adsorbed thereon, a desorbent is brought into contact with the adsorbent containing para-xylene to allow para-xylene to be desorbed therefrom, and a mixture of the desorbent and para-xylene is subjected to separation in a distillation column. Thus, para-xylene can be obtained at a high concentration.

<Circulation Step>

The gas phase having been extracted from the gas-liquid separator contains carbon dioxide, carbon monoxide, and hydrogen as unreacted gases, and hence these gases are returned to an inlet side of a heater in the previous stage of the reactor and circulated into the reactor. However, the gas phase contains lower alkanes (mainly methane) each having 1 to 4 carbon atoms as by-products in addition to those unreacted gases. Such lower alkanes hardly contribute to the para-xylene synthesis reaction in the reactor, and hence these lower alkanes are gradually accumulated in the gas in a circulation path. In view of the foregoing, it is required to purge part of the gas in the circulation path to an outside. When about 1 vol % to about 20 vol % of the entire circulation amount is purged, the concentration of the lower alkanes in the circulation path can be maintained at less than 40 vol %.

<Other Accompanying Steps>

In order to increase the production of para-xylene, isomerization treatment or disproportionation treatment is desirably performed as required. Ortho-xylene and meta-xylene, which remain after high-purity para-xylene is obtained in the purification step, may be subjected to isomerization treatment to convert part thereof to para-xylene, and then be returned to an inlet side of the purification step. Specifically, a mixture of ortho-xylene and meta-xylene from which para-xylene has been separated is subjected to isomerization treatment by being heated and caused to pass through a reactor having a zeolite catalyst packed therein.

In addition, toluene or trimethylbenzene, which has been separated through distillation, may be subjected to disproportionation treatment to convert part thereof to a xylene mixture containing para-xylene, and then be returned to the inlet side of the purification step. Specifically, a mixture containing toluene or trimethylbenzene is subjected to disproportionation treatment by being heated and caused to pass through a reactor having a zeolite catalyst packed therein.

The gas having been purged in the circulation step contains, in addition to carbon dioxide, which is an unreacted gas, carbon monoxide and hydrogen, and lower alkanes as well, and hence may be used as a fuel gas. However, in order to reduce the amount of hydrogen required as a raw material gas, it is preferred to separate hydrogen contained in the purge gas through membrane separation, adsorption separation (pressure swing adsorption or the like), or the like to recover only hydrogen from the purge gas, and recycle hydrogen.

In addition, as well as hydrogen, carbon dioxide or carbon monoxide may be recovered from the purge gas. Those gases can be separated and recovered from the purge gas by performing membrane separation with an appropriate membrane.

It is preferred that the heating of the raw material mixed gas performed at an inlet side of the reactor and the cooling of the product gas mixture performed at an outlet side of the reactor be performed so that heat recovered through the cooling of the product gas mixture is used for the heating of the raw material mixed gas because energy required for the heating and the cooling can be saved. In addition, when sufficient cooling of the product gas mixture cannot be expected only through heat exchange, the product gas mixture may be further cooled after having been reduced in temperature to some extent through a heat exchange operation.

EXAMPLES

First Embodiment

FIG. 1 is a diagram for illustrating an example of an apparatus suitable for performing the method of the present invention. In the method of the present invention, the raw material mixed gas is heated in a heater 1, and is then introduced into a reactor 2. A catalyst containing an oxide of at least one kind of metal selected from chromium, zinc, and copper and a catalyst containing ZSM-5-based zeolite coated with silicalite-1 are mixed and packed in the reactor 2 to form a layer of a mixed catalyst, and the raw material gas mixture introduced into the reactor is brought into contact with the mixed catalyst in the reactor under a high temperature and high pressure atmosphere at 250° C. to 600° C. and 1 MPaG to 10 MPaG to cause a reaction, to thereby become the product gas mixture containing para-xylene (reaction step).

The obtained product gas mixture is cooled to around normal temperature in a cooler 3, and introduced into a gas-liquid separator 4. The high boiling point component having been condensed is separated into three phases in the gas-liquid separator, that is, the water phase (lower layer) containing a water-soluble component, the oil phase (middle layer) containing para-xylene, and the gas phase (upper layer) containing an unreacted gas (separation step).

After having been extracted from the gas-liquid separator 4, the oil phase forming the middle layer is first subjected to a purification step 5 based on a combination of distillation separation, adsorption separation, isomerization treatment, and disproportionation treatment. Thus, target high-purity para-xylene can be obtained, and the amount of para-xylene can be increased as compared to that at an outlet of the gas-liquid separator 4 (purification step).

The gas phase forming the upper layer contains unreacted gases, such as hydrogen, carbon dioxide, and carbon monoxide. Accordingly, after having been extracted from the gas-liquid separator 4, the gas phase is mixed as a circulation gas into the flow of the raw material mixed gas at an inlet side of the heater 1, and is heated again and returned to the reactor 2. Part of the circulation gas is purged outside a system in order to prevent accumulation of lower alkanes (circulation step).

The water phase forming the lower layer is transferred to a wastewater treatment device 6 and treated therein in order to remove a water-soluble organic substance or the like. Meanwhile, a purge gas, which is obtained by extracting part of the circulation gas, is effectively utilized as a fuel gas, for example, as a heat source for a nearby heating furnace.

Second Embodiment

Figure 2:
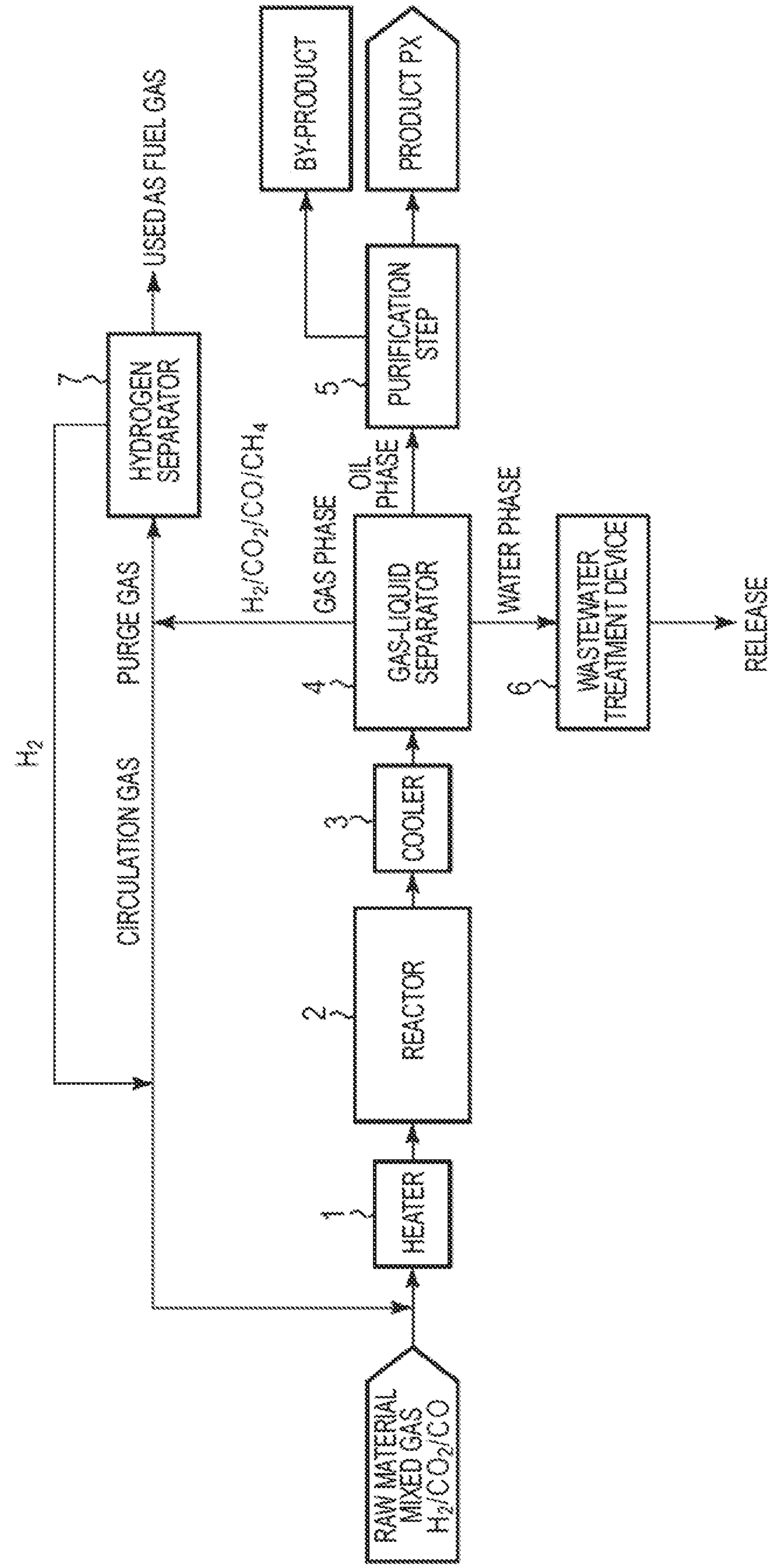
FIG. 2 is a diagram for illustrating a second embodiment of the apparatus suitable for performing the method of the present invention.

FIG. 2 is a diagram for illustrating another example of the apparatus suitable for performing the method of the present invention. The apparatus of FIG. 2 has the same basic configuration as the apparatus of FIG. 1, but differs therefrom in that hydrogen is separated from the purge gas and joined to the circulation gas. FIG. 2 is described below, but the description of the same configuration as that of FIG. 1 is omitted.

The purge gas contains lower alkyls (methane, ethane, propane, and the like), which are reaction by-products, in small amounts, in addition to unreacted carbon dioxide, carbon monoxide, and hydrogen. Those lower alkyls do not contribute to the para-xylene synthesis reaction in the reactor, and are hence required to be extracted as the purge gas in order to prevent accumulation thereof in the circulation gas. Meanwhile, hydrogen contained in the purge gas can be recovered by a hydrogen separator 7 based on membrane separation using a hydrogen separation membrane, adsorption separation (pressure swing adsorption or the like), or the like. Accordingly, hydrogen can be reutilized as a raw material by recovering only hydrogen from the purge gas, joining hydrogen again to the circulation gas, and returning hydrogen to the reactor.

In the apparatus of FIG. 2, as an alternative to using the entire amount of the purge gas as a fuel gas, a large part of hydrogen contained therein is reutilized as a raw material gas, which leads to a reduction in usage amount of raw material hydrogen.

Third Embodiment

Figure 3:
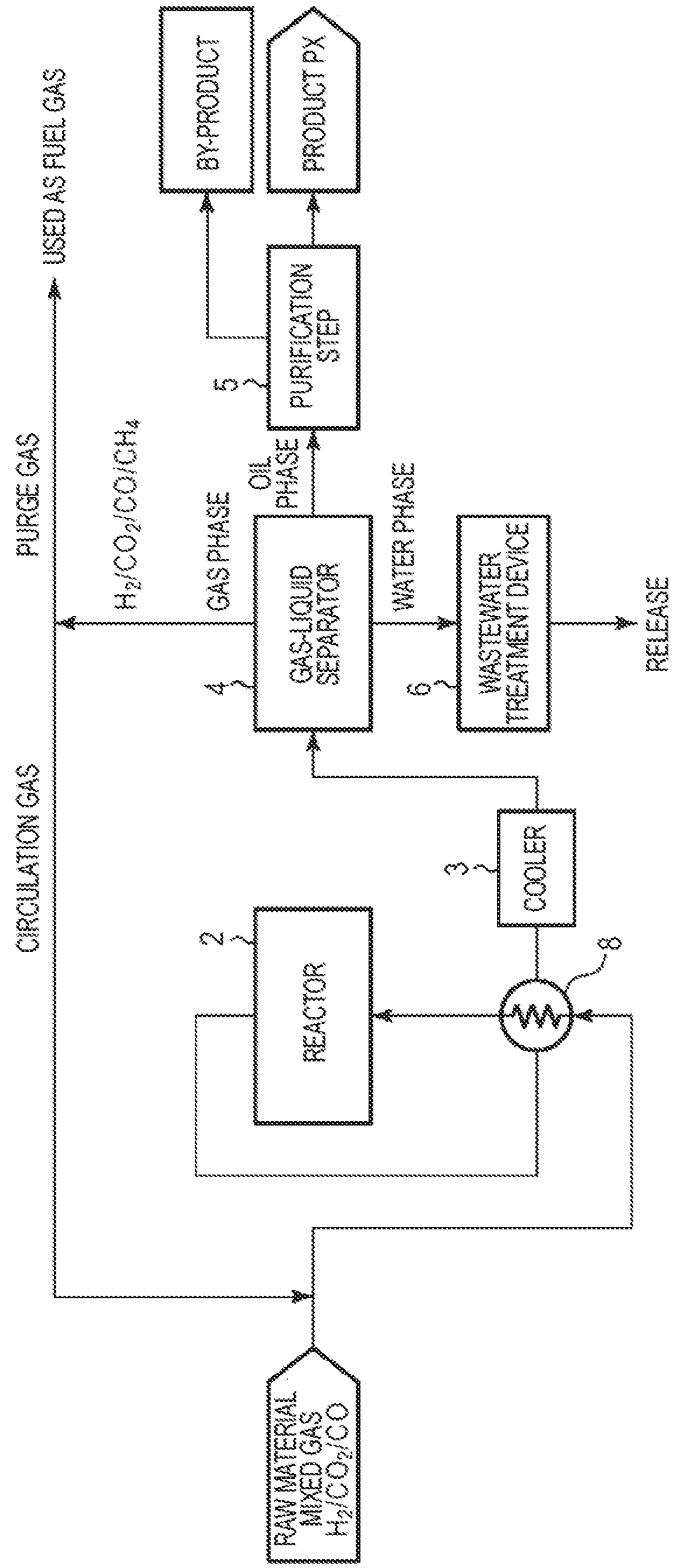
FIG. 3 is a diagram for illustrating a third embodiment of the apparatus suitable for performing the method of the present invention.

FIG. 3 is a diagram for illustrating still another example of the apparatus suitable for performing the method of the present invention. The apparatus of FIG. 3 has the same basic configuration as the apparatus of FIG. 1, but differs therefrom in that the heating (preheating) of the raw material mixed gas and the cooling of the product gas mixture are performed with a heat exchanger 8. FIG. 3 is described below, but the description of the same configuration as that of FIG. 1 is omitted.

One of the objects of the present invention is to achieve a reduction in concentration of carbon dioxide in the atmosphere by using carbon dioxide as a raw material for producing para-xylene. Accordingly, it is required that a carbon dioxide emission amount and an accompanying energy consumption amount in the process of the present invention be reduced to the extent possible. The apparatus of FIG. 3 is intended to reduce the amount of a heat source (steam, a fuel gas, or the like), which is required to be loaded from an outside for the heating of the raw material mixed gas.

The apparatus of FIG. 3 is configured to combine a lead-in flow passage of the raw material mixed gas to the reactor and a lead-out flow passage of the product gas mixture from the reactor with each other via the heat exchanger 8, to thereby use a heat amount obtained through the cooling of the product gas mixture for the heating of the raw material mixed gas. A general shell and tube-type heat exchanger may be used as the heat exchanger.

Fourth Embodiment

Figure 4:
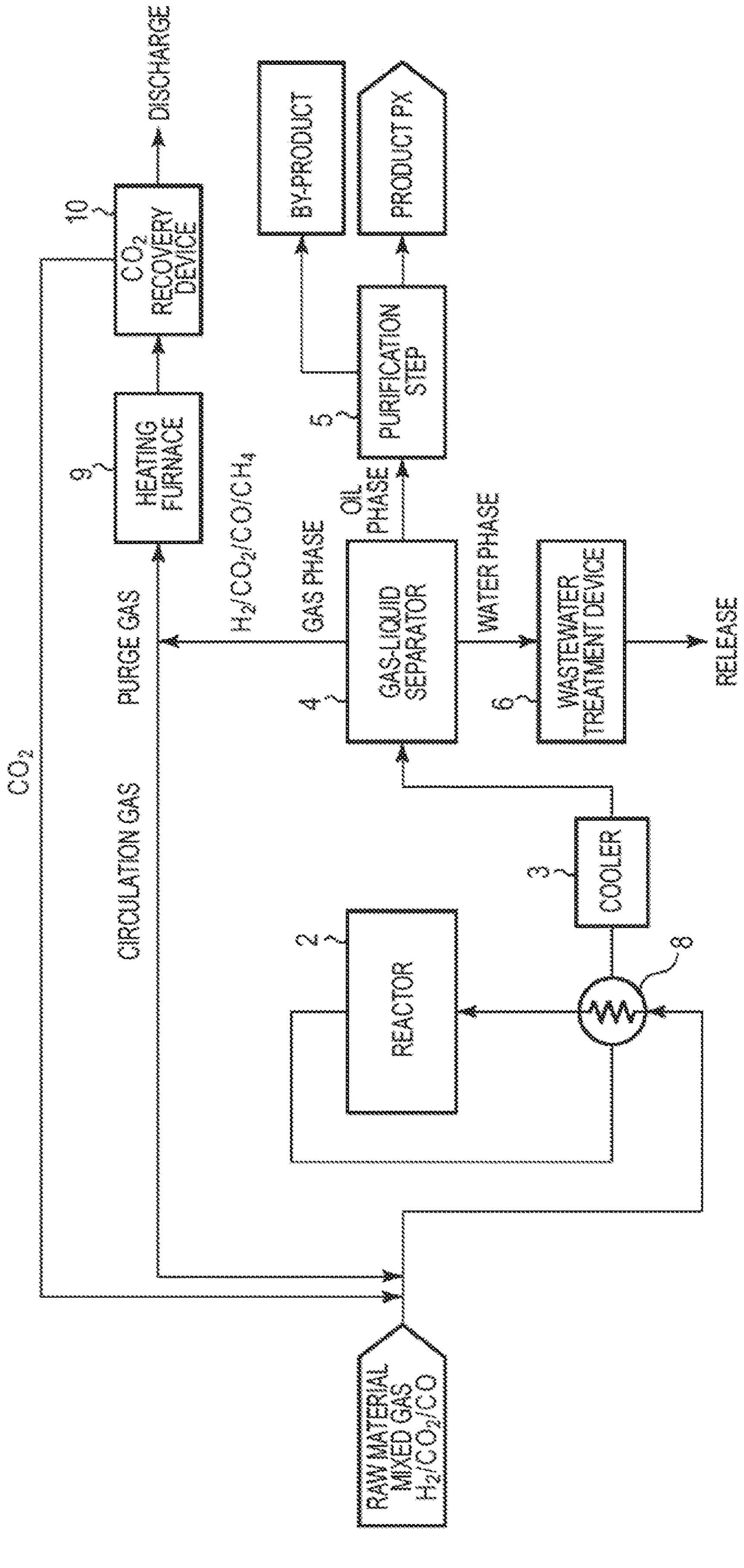
FIG. 4 is a diagram for illustrating a fourth embodiment of the apparatus suitable for performing the method of the present invention.

FIG. 4 is a diagram for illustrating yet still another example of the apparatus suitable for performing the method of the present invention. The apparatus of FIG. 4 has the same basic configuration as the apparatus of FIG. 3, but differs therefrom in that the purge gas from the circulation gas is combusted in a nearby heating furnace 9 or the like, and only $CO_2$ is then separated and recovered by a $CO_2$ recovery device 10, and is recycled as part of a raw material gas.

In an embodiment of FIG. 4, $CO_2$ after the combustion of the purge gas is also recovered as a raw material, which contributes considerably to a reduction in overall carbon dioxide emission amount.

Example 1

Figure 5:
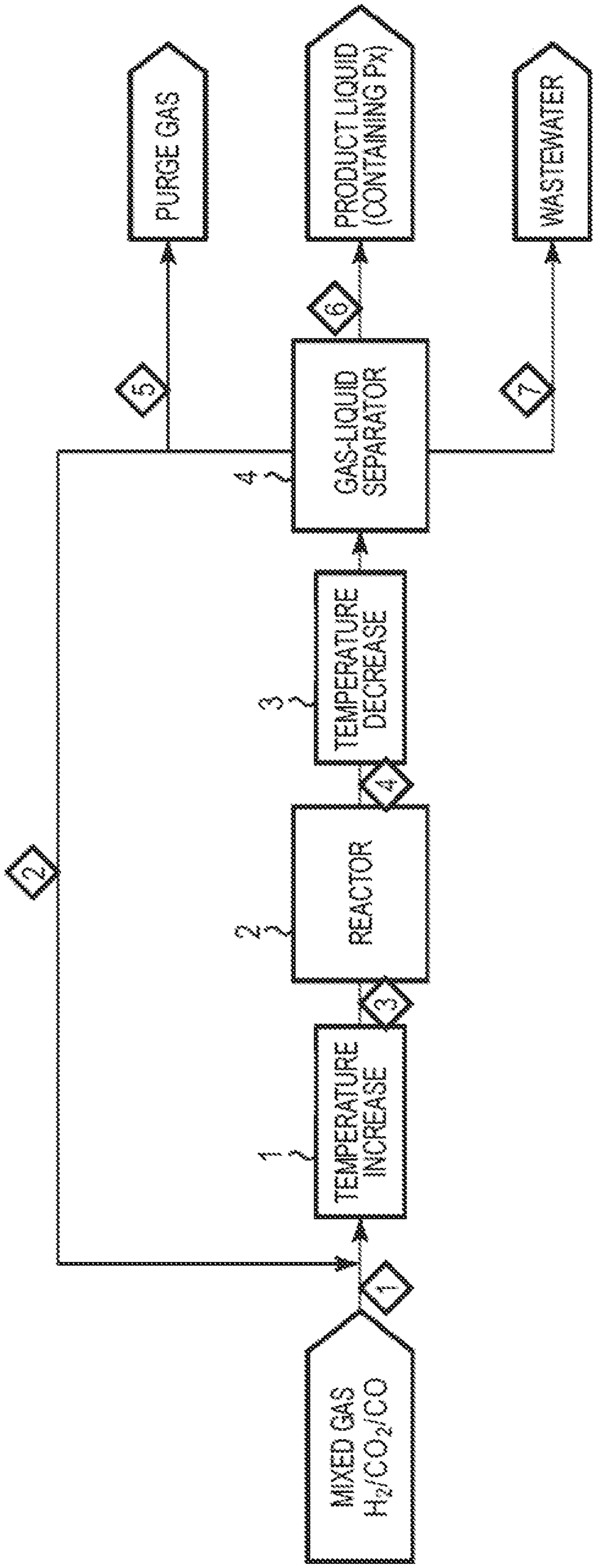
FIG. 5 is a process flow assumed in simulation of each of Examples 1 and 2.

A process flow having the configuration illustrated in FIG. 5 was assumed, and a case of producing para-xylene at 12,500 kg/h (100,000 ton/yr) through use of a raw material mixed gas formed of carbon dioxide and hydrogen was simulated. The results of the simulation are shown in Table 1 as temperatures, pressures, flow rates, and compositions at the respective points 1 to 7 of FIG. 5.

Example 2

A process flow having the configuration illustrated in FIG. 5 was assumed, and a case of producing para-xylene at 12,500 kg/h (100,000 ton/yr) through use of a raw material mixed gas formed of carbon monoxide and hydrogen was simulated. The results of the simulation are shown in Table 2 as temperatures, pressures, flow rates, and compositions at the respective points 1 to 7 of FIG. 5.

Example 3

Figure 6:
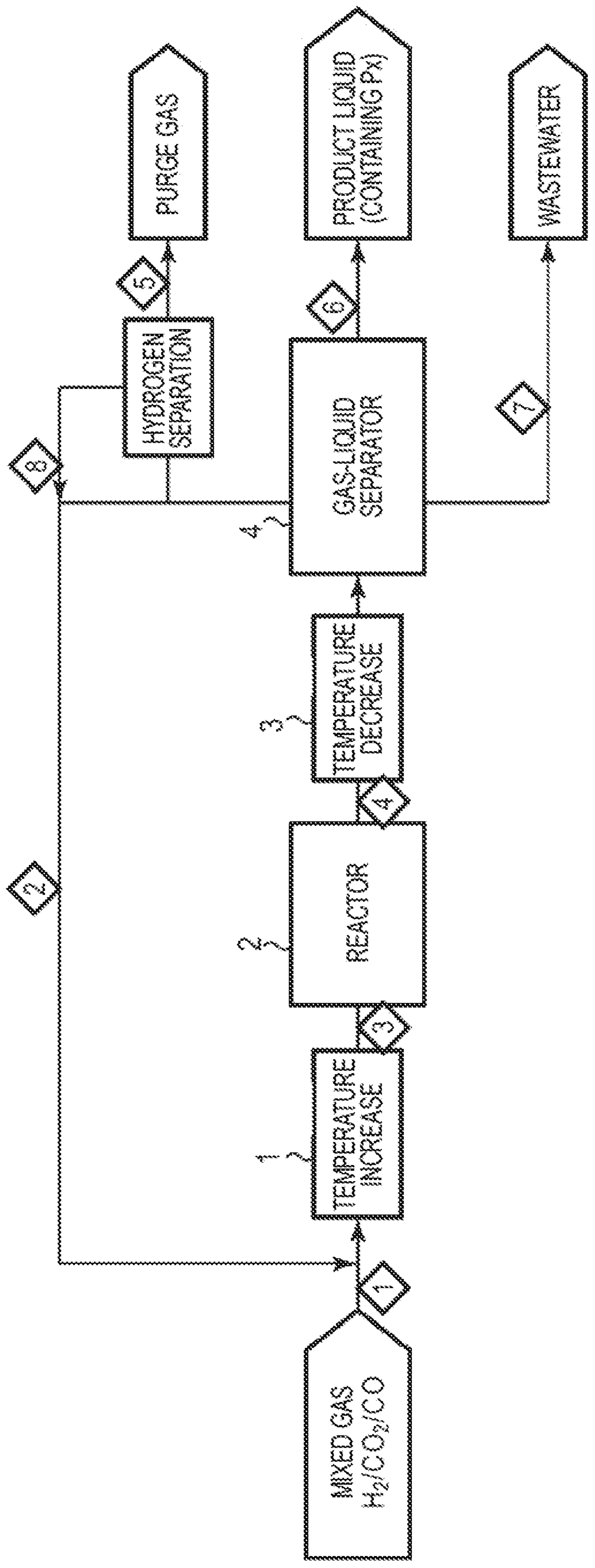
FIG. 6 is a process flow assumed in simulation of Example 3.

A process flow having the configuration illustrated in FIG. 6 was assumed, and a case of producing para-xylene at 12,500 kg/h (100,000 ton/yr) through use of a raw material mixed gas formed of carbon dioxide and hydrogen was simulated. The results of the simulation are shown in Table 3 as temperatures, pressures, flow rates, and compositions at the respective points 1 to 8 of FIG. 6.

TABLE 1

| Example 1 $CO_2/H_2$ supply | Position number | | | | | | |
|---|---|---|---|---|---|---|---|
| | 1 | 2 | 3 | 4 | 5 | 6 | 7 |
| Flow phase | Gas phase flow | Gas phase flow | Gas phase flow | Gas phase flow | Gas phase flow | Liquid phase flow | Liquid phase flow |
| Temperature (° C.) | 20 | 54 | 300 | 344 | 40 | 40 | 40 |
| Pressure (kPaG) | 4,300 | 4,300 | 4,200 | 4,000 | 3,850 | 3,850 | 3,850 |
| Molecular weight | 13.6 | 18 | 17.3 | 18.4 | 18 | 94.8 | 18.1 |
| Mass flow rate (ton/h) | 153 | 1,016 | 1,169 | 1,169 | 39 | 24 | 90 |
| Molar flow rate (kgmol/h) | 11,274 | 56,366 | 67,640 | 63,722 | 2,141 | 263 | 4,952 |
| Weight fraction | | | | | | | |
| $H_2$ | 0.107 | 0.055 | 0.062 | 0.050 | 0.055 | 0.000 | 0.000 |
| CO | 0.000 | 0.119 | 0.104 | 0.107 | 0.119 | 0.001 | 0.000 |
| $CO_2$ | 0.893 | 0.590 | 0.630 | 0.534 | 0.590 | 0.036 | 0.009 |
| $H_2O$ | 0.000 | 0.002 | 0.002 | 0.078 | 0.002 | 0.001 | 0.991 |
| $CH_4$ | 0.000 | 0.128 | 0.111 | 0.115 | 0.128 | 0.003 | 0.000 |
| $C_2$-$C_4$ paraffins | 0.000 | 0.095 | 0.082 | 0.086 | 0.095 | 0.037 | 0.000 |
| $C_2$-$C_4$ olefins | 0.000 | 0.002 | 0.001 | 0.002 | 0.002 | 0.001 | 0.000 |
| $C_5$ + hydrocarbons | 0.000 | 0.003 | 0.003 | 0.003 | 0.003 | 0.009 | 0.000 |
| Benzene | 0.000 | 0.000 | 0.000 | 0.000 | 0.000 | 0.003 | 0.000 |
| Toluene | 0.000 | 0.001 | 0.001 | 0.003 | 0.001 | 0.070 | 0.000 |
| Ethylbenzene | 0.000 | 0.000 | 0.000 | 0.000 | 0.000 | 0.013 | 0.000 |
| O-xylene | 0.000 | 0.000 | 0.000 | 0.001 | 0.000 | 0.042 | 0.000 |
| M-xylene | 0.000 | 0.000 | 0.000 | 0.001 | 0.000 | 0.016 | 0.000 |
| P-xylene | 0.000 | 0.004 | 0.003 | 0.014 | 0.004 | 0.511 | 0.000 |
| $C_9$ aromatics | 0.000 | 0.000 | 0.001 | 0.005 | 0.000 | 0.234 | 0.000 |
| $C_{10}$ aromatics | 0.000 | 0.001 | 0.000 | 0.001 | 0.001 | 0.023 | 0.000 |

TABLE 2

| Example 2 $CO/H_2$ supply | Position number | | | | | | |
|---|---|---|---|---|---|---|---|
| | 1 | 2 | 3 | 4 | 5 | 6 | 7 |
| Flow phase | Gas phase flow | Gas phase flow | Gas phase flow | Gas phase flow | Gas phase flow | Liquid phase flow | Liquid phase flow |
| Temperature (° C.) | 20 | 53 | 300 | 345 | 40 | 40 | 40 |
| Pressure (kPaG) | 4,300 | 4,300 | 4,200 | 4,000 | 3,850 | 3,850 | 3,850 |
| Molecular weight | 11.9 | 25.0 | 22.8 | 25.1 | 25.0 | 86.8 | 18.2 |
| Mass flow rate (ton/h) | 78 | 731 | 809 | 809 | 13 | 28 | 37 |
| Molar flow rate (kgmol/h) | 6,538 | 32,677 | 39,215 | 35,608 | 566 | 297 | 2,068 |
| Weight fraction | | | | | | | |
| $H_2$ | 0.105 | 0.024 | 0.032 | 0.022 | 0.024 | 0.000 | 0.000 |
| CO | 0.895 | 0.069 | 0.149 | 0.064 | 0.069 | 0.001 | 0.000 |
| $CO_2$ | 0.000 | 0.567 | 0.512 | 0.523 | 0.567 | 0.043 | 0.010 |
| $H_2O$ | 0.000 | 0.002 | 0.002 | 0.048 | 0.002 | 0.001 | 0.990 |
| $CH_4$ | 0.000 | 0.249 | 0.225 | 0.229 | 0.249 | 0.007 | 0.000 |
| $C_2$-$C_4$ paraffins | 0.000 | 0.079 | 0.071 | 0.074 | 0.079 | 0.037 | 0.000 |
| $C_2$-$C_4$ olefins | 0.000 | 0.001 | 0.001 | 0.001 | 0.001 | 0.001 | 0.000 |

TABLE 2-continued

| Example 2 CO/$H_2$ supply | | | | | | | |
|---|---|---|---|---|---|---|---|
| | Position number | | | | | | |
| | 1 | 2 | 3 | 4 | 5 | 6 | 7 |
| $C_5$ + hydrocarbons | 0.000 | 0.004 | 0.003 | 0.004 | 0.004 | 0.012 | 0.000 |
| Benzene | 0.000 | 0.000 | 0.000 | 0.000 | 0.000 | 0.002 | 0.000 |
| Toluene | 0.000 | 0.001 | 0.001 | 0.002 | 0.001 | 0.044 | 0.000 |
| Ethylbenzene | 0.000 | 0.000 | 0.000 | 0.000 | 0.000 | 0.011 | 0.000 |
| O-xylene | 0.000 | 0.000 | 0.000 | 0.001 | 0.000 | 0.037 | 0.000 |
| M-xylene | 0.000 | 0.000 | 0.000 | 0.001 | 0.000 | 0.014 | 0.000 |
| P-xylene | 0.000 | 0.003 | 0.003 | 0.018 | 0.003 | 0.450 | 0.000 |
| $C_9$ aromatics | 0.000 | 0.001 | 0.001 | 0.011 | 0.001 | 0.291 | 0.000 |
| $C_{10}$ aromatics | 0.000 | 0.000 | 0.000 | 0.002 | 0.000 | 0.049 | 0.000 |

TABLE 3

| Example 3 $CO_2$/$H_2$ supply | | | | | | | | |
|---|---|---|---|---|---|---|---|---|
| | Position number | | | | | | | |
| | 1 | 2 | 3 | 4 | 5 | 6 | 7 | 8 |
| Flow phase | Gas phase flow | Gas phase flow | Gas phase flow | Gas phase flow | Gas phase flow | Liquid phase flow | Liquid phase flow | Gas phase flow |
| Temperature (° C.) | 20 | 54 | 300 | 344 | 40 | 40 | 40 | 40 |
| Pressure (kPaG) | 4,300 | 4,300 | 4,200 | 4,000 | 50 | 3,850 | 3,850 | 3,700 |
| Molecular weight | 14.5 | 17.8 | 17.3 | 18.4 | 28.5 | 94.8 | 18.1 | 2 |
| Mass flow rate (ton/h) | 151 | 1,018 | 1,169 | 1,169 | 37 | 24 | 90 | 2 |
| Molar flow rate (kgmol/h) | 10,426 | 57,214 | 67,640 | 63,722 | 1,293 | 263 | 4,952 | 848 |
| Weight fraction | | | | | | | | |
| $H_2$ | 0.097 | 0.057 | 0.062 | 0.050 | 0.012 | 0.000 | 0.000 | 1.000 |
| CO | 0.000 | 0.119 | 0.104 | 0.107 | 0.125 | 0.001 | 0.000 | 0.000 |
| $CO_2$ | 0.903 | 0.590 | 0.630 | 0.534 | 0.618 | 0.036 | 0.009 | 0.000 |
| $H_2O$ | 0.000 | 0.002 | 0.002 | 0.078 | 0.002 | 0.001 | 0.991 | 0.000 |
| $CH_4$ | 0.000 | 0.127 | 0.111 | 0.115 | 0.133 | 0.003 | 0.000 | 0.000 |
| $C_2$-$C_4$ paraffins | 0.000 | 0.094 | 0.082 | 0.086 | 0.099 | 0.037 | 0.000 | 0.000 |
| $C_2$-$C_4$ olefins | 0.000 | 0.002 | 0.001 | 0.002 | 0.002 | 0.001 | 0.000 | 0.000 |
| $C_5$ + hydrocarbons | 0.000 | 0.003 | 0.003 | 0.003 | 0.003 | 0.009 | 0.000 | 0.000 |
| Benzene | 0.000 | 0.000 | 0.000 | 0.000 | 0.000 | 0.003 | 0.000 | 0.000 |
| Toluene | 0.000 | 0.001 | 0.001 | 0.003 | 0.001 | 0.070 | 0.000 | 0.000 |
| Ethylbenzene | 0.000 | 0.000 | 0.000 | 0.000 | 0.000 | 0.013 | 0.000 | 0.000 |
| O-xylene | 0.000 | 0.000 | 0.000 | 0.001 | 0.000 | 0.042 | 0.000 | 0.000 |
| M-xylene | 0.000 | 0.000 | 0.000 | 0.001 | 0.000 | 0.016 | 0.000 | 0.000 |
| P-xylene | 0.000 | 0.004 | 0.003 | 0.014 | 0.004 | 0.511 | 0.000 | 0.000 |
| $C_9$ aromatics | 0.000 | 0.001 | 0.001 | 0.005 | 0.001 | 0.234 | 0.000 | 0.000 |
| $C_{10}$ aromatics | 0.000 | 0.000 | 0.000 | 0.001 | 0.000 | 0.023 | 0.000 | 0.000 |

This application claims the benefit of priority from Japanese Patent Application No. 2021-78065, filed on Apr. 30, 2021, the content of which is incorporated herein by reference.

REFERENCE SIGNS LIST

1 heater
2 reactor
3 cooler
4 gas-liquid separator
5 purification step
6 wastewater treatment device
7 hydrogen separator
8 heat exchanger
9 heating furnace
10 $CO_2$ recovery device

The invention claimed is:

1. A method of producing para-xylene using, as a main raw material, a mixed gas of carbon dioxide or carbon monoxide or both thereof and hydrogen, the method comprising:

a reaction step of bringing a raw material mixed gas including the mixed gas into contact with a reaction catalyst under high temperature and high pressure to cause a reaction, to thereby obtain a product gas mixture containing para-xylene;

a separation step of cooling the product gas mixture obtained in the reaction step to condense a high boiling point component, to thereby separate the product gas mixture into a water phase containing a water-soluble component, an oil phase containing a xylene mixture, and a gas phase containing an unreacted gas; and a circulation step of mixing at least part of the gas phase having been separated in the separation step into the raw material mixed gas, wherein the separation step comprises first separating a gas-liquid mixture obtained by cooling the product gas mixture into a liquid phase and the gas phase, and then separating the liquid phase having been separated into the oil phase and the water phase by a separation method utilizing a difference in specific gravity, and wherein the circulation step comprises purging part of a circulation gas, followed by mixing hydrogen having been separated and recovered from the resultant purge gas, using pressure swing adsorption (PSA) or a hydrogen separation membrane for hydrogen from the purge gas, into the raw material mixed gas.

2. The method according to claim 1, wherein the reaction catalyst used in the reaction step is a mixed catalyst including a mixture of: a catalyst containing an oxide of at least one kind of metal selected from chromium, zinc, and copper; and a catalyst containing ZSM-5-based zeolite having a surface coated with a compound containing silicon.

3. The method according to claim 1, wherein the reaction step comprises bringing the raw material mixed gas into contact with the reaction catalyst at a reaction temperature of from 250° C. to 600° C. and a reaction pressure of from 1 MPaG to 10 MPaG.

4. The method according to claim 1, wherein the circulation step comprises purging part of a circulation gas to effectively utilize the resultant purge gas as a fuel gas.

5. The method according to claim 1, wherein the method comprises heat exchanging the raw material mixed gas and the product gas mixture, followed by transferring the raw material mixed gas to the reaction step.

6. The method according to claim 1, wherein the method comprises using, as at least part of carbon dioxide forming the raw material mixed gas, carbon dioxide separated from a combustion exhaust gas of a thermal power plant or a heating furnace, carbon dioxide separated in an ammonia production apparatus, an ethylene glycol production apparatus, or a hydrogen production apparatus, carbon dioxide separated from a product gas of a gasification furnace for coal, biomass, or garbage, carbon dioxide separated from a blast furnace of an ironworks, or carbon dioxide separated from air in an atmosphere.

7. The method according to claim 1, wherein the method comprises using, as at least part of hydrogen forming the raw material mixed gas, hydrogen generated through electrolysis of water with electric power generated by solar power, wind power, water power, geothermal power, biomass, or nuclear power.

8. The method according to claim 1, wherein the method comprises using, as at least part of the raw material mixed gas, a synthesis gas generated from a gasification furnace, an off-gas discharged from a blast furnace of an ironworks, an off-gas separated in a hydrogen production apparatus, a synthesis gas generated through co-electrolysis of water and carbon dioxide, or a synthesis gas generated through a reverse shift reaction between hydrogen and carbon dioxide.

* * * * *